United States Patent
Zhang et al.

(10) Patent No.: US 10,188,834 B2
(45) Date of Patent: Jan. 29, 2019

(54) ADJUSTABLE BENT SHEATH TUBE

(71) Applicant: Lifetech Scientific (Shenzhen) Co., Ltd., Shenzhen (CN)

(72) Inventors: Tingchao Zhang, Shenzhen (CN); Yang Li, Shenzhen (CN); Gang Wang, Shenzhen (CN); Deyuan Zhang, Shenzhen (CN); Weiguo Fu, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 76 days.

(21) Appl. No.: 15/107,836

(22) PCT Filed: Dec. 24, 2014

(86) PCT No.: PCT/CN2014/094826
§ 371 (c)(1),
(2) Date: Jun. 23, 2016

(87) PCT Pub. No.: WO2015/096740
PCT Pub. Date: Jul. 2, 2015

(65) Prior Publication Data
US 2016/0317784 A1    Nov. 3, 2016

(30) Foreign Application Priority Data
Dec. 27, 2013   (CN) .......................... 2013 1 0740058

(51) Int. Cl.
*A61M 25/01*   (2006.01)
*A61M 25/06*   (2006.01)
*A61M 25/00*   (2006.01)

(52) U.S. Cl.
CPC .... *A61M 25/0147* (2013.01); *A61M 25/0662* (2013.01); *A61M 25/0009* (2013.01); *A61M 2025/015* (2013.01)

(58) Field of Classification Search
CPC .......... A61M 25/0147; A61M 25/0662; A61M 2025/015; A61M 25/0009
See application file for complete search history.

(56) References Cited

U.S. PATENT DOCUMENTS 5,383,852 A    1/1995   Stevens
6,547,757 B1   4/2003   Kranz
(Continued)

FOREIGN PATENT DOCUMENTS

CN    100548409       10/2009
CN    100548409 C     10/2009
(Continued)

OTHER PUBLICATIONS

Office action in parent priority application 201310740058.5 in China dated Feb. 25, 2015.
(Continued)

*Primary Examiner* — Nathan R Price
*Assistant Examiner* — Dung Ulsh
(74) *Attorney, Agent, or Firm* — Raymond Sun (57) ABSTRACT

The present invention relates to a steerable sheath tube (100) including a tube body (110), a traction mechanism (120) and a fixing and connecting mechanism (130). The traction mechanism (120) includes an anchor ring (121) and a traction wire (122). The anchor ring (121) is coaxially embedded in a distal elastic segment (111) of the tube body (110). The traction wire (122) is arranged in a side wall of the tube body (110), and extends along the axial direction of the tube body (110). The traction wire (122) includes a first segment and a second segment connected to each other, wherein the first segment is connected to the fixing and connecting mechanism (130) near a proximal end of the tube body (110), and the second segment hooks the anchor ring (121).

9 Claims, 5 Drawing Sheets

(56) References Cited

U.S. PATENT DOCUMENTS

| | | | |
|---|---|---|---|
| 2001/0025134 A1* | 9/2001 | Bon | A61M 25/0136 600/146 |
| 2005/0070844 A1 | 3/2005 | Chow et al. | |
| 2005/0075661 A1* | 4/2005 | Levine | A61M 25/008 606/194 |
| 2006/0100640 A1* | 5/2006 | Bolduc | A61B 17/00234 606/108 |
| 2006/0271078 A1* | 11/2006 | Modesitt | A61B 17/0057 606/167 |
| 2007/0299424 A1* | 12/2007 | Cumming | A61M 25/0012 604/527 |
| 2009/0024110 A1* | 1/2009 | Heideman | A61M 25/0012 604/528 |
| 2013/0158478 A1 | 6/2013 | Kaufmann et al. | |
| 2013/0281925 A1* | 10/2013 | Benscoter | A61B 1/0125 604/95.04 |
| 2016/0051278 A1* | 2/2016 | Jacobs | A61B 17/32056 606/113 |
| 2016/0367787 A1* | 12/2016 | Van Hoven | A61M 25/0147 |
| 2017/0296777 A1* | 10/2017 | Heisel | A61M 25/0012 |

FOREIGN PATENT DOCUMENTS

| | | |
|---|---|---|
| DE | 38 19 372 C1 | 1/1990 |
| WO | WO 97/29801 A1 | 8/1997 |
| WO | WO 2005/123169 A1 | 12/2005 |

OTHER PUBLICATIONS

Office action in parent priority application 201310740058.5 in China dated Oct. 26, 2015.
First Office Action for corresponding China Application No. 201310740058.5.
Second Office Action for corresponding China Application No. 201310740058.5.
Supplementary European Search Report dated Jul. 25, 2017 for corresponding European Application No. EP 14 87 4604.

* cited by examiner

ADJUSTABLE BENT SHEATH TUBE

TECHNICAL FIELD

The present invention relates to medical devices, in particular to an adjustable bend sheath tube.

BACKGROUND OF THE PRESENT INVENTION

A medical sheath tube that is used in minimally invasive diagnosis and treatment surgery is configured to establish passages, deliver or withdraw instruments, deliver drugs, or guide body fluid out, etc. An adjustable bend sheath tube with an adjustable bend at the distal end may reach a target diseased position quickly and reliably to reduce the operation time. In the minimally invasive interventional field, one end relatively far away from an operator is usually defined as a distal end, and the other end relatively close to the operator is defined as a proximal end.

U.S Patent document U.S. Pat. No. 6,945,956B2 disclosed an adjustable bend sheath tube, including a tube body, a traction mechanism and a handle having a control system; the traction mechanism includes a radiopaque ring annularly arranged in a side wall of a distal elastic segment of the tube body, and a traction wire arranged in the side wall of the tube body; a distal end of the traction wire is directly fixed on a ring wall of the radiopaque ring by welding, and a proximal end of the traction wire is connected to the control system. The traction wire is pulled by the control system, the force and displacement are transferred to the traction wire to drive the traction wire to relatively move in the axial direction of the tube body, and then the force and displacement are transferred to the radiopaque ring through welding points to drive the distal elastic segment of the tube body to be bent, thereby achieving adjustable bending of the distal end of the tube body.

According to the requirements imposed on the diameter size and angle range of the adjustable bend sheath tube, when reaching a maximum adjustable bending angle, the tensile force applied onto the traction wire is generally larger, which may reach a maximum of 5 Kgf. If a larger instrument is delivered with the distal end of the sheath being bent, the instrument will apply a certain back tensile force to a bent channel, so that the tensile force applied on the traction wire is larger, thereby putting forward higher requirements on the tensile strength of a traction system. In general, it is better for the inner diameter of a medical sheath tube to be larger, and for the outer diameter thereof to be smaller. The smaller outer diameter may reduce the damage to the human blood vessels, and the larger inner diameter allows larger instruments to be delivered, thus requiring that the tube wall of the tube body must be as thin as possible; i.e., requiring that the volume of a portion of the traction system disposed in the tube wall must be as small as possible, in order to be covered in the tube wall and to reduce the thickness of the tube wall. The doctor will carry out the adjustable bending operation repeatedly before and during surgery, and is required to continuously and accurately adjust the angle of the distal end of the tube body, in order to enable the bending angle to adapt to the complex anatomical structure of the lumen in different human bodies. The traction system is required to have outstanding tensile fatigue performance for adjustable bending. Therefore, the tensile strength, the tensile fatigue strength and the wall thickness of the tube body, are all crucial to an adjustable bend sheath tube.

The traction wire is usually thin, and the corresponding welding area is small, thus not only resulting in great difficulty during the welding process, but also leading to stress concentration of the welding point, change of the section size, change of the surface morphology, residual stress, and so on. Moreover, according to the theory of metal welding, it is known that the physical strength after welding is only half or less of that during non-welding, so that the material strength is decreased significantly, thus resulting in insufficient tensile strength and low reliability of the traction wire. Not only is the welding process difficult to control, but also the procedure qualification rate in the process is low. In addition, the welding point has an increased fracture risk, the portion with welding points under a larger traction force or after being bent repeatedly can be fractured very easily, so that the product then lacks an adjustable bending function, thereby resulting in failure of the surgery and even injury to the human body. Furthermore, the welding is a rigid connection, which is difficult to meet the requirement of repeated adjustable bending, and the fatigue strength is poor. If a thicker traction wire were utilized, the wall thickness of the tube body would be increased, thereby greatly reducing the possibility of successfully entering target blood vessels and also reducing flexibility of the tube body.

In view of this, U.S. Patent document U.S. Pat. No. 7,553,305B2 adopts a fixed anchor to implement a part of the functions of the radiopaque ring. The fixed anchor is connected to the distal end of the traction wire and located within the side wall of the tube body, and at least one end has a rim around the axial direction of the traction wire. When the traction wire is pulled, the traction force is transferred to the fixed anchor, and the fixed anchor acts as a force bearing body to drive the tail end of the tube body so as to achieve the adjustable bending function.

The fixed anchor has a rim unfolding around the radial direction of the traction wire. Due to the large diameter of the rim, the side wall should have sufficient thickness to completely cover the fixed anchor. However, the medical sheath tube requires that the wall thickness of the tube body should be as small as possible. The rim will certainly increase the wall thickness of the sheath tube. In the case of a fixed size of a delivery lumen, if the outer diameter of the tube body is larger, the injury to the human body during delivery of the instrument of the same specification into the human body is greater. Moreover, the fixed anchor is a longitudinal structure along the axial direction of the tube body, and the distal end of the tube body opposite to the fixed anchor is also provided with a radiopaque ring, so that the length of a distal rigid segment of the tube body is increased and the flexibility of an elastic adjustable bend segment is reduced; when the distal end of the tube body is bent to a certain angle, compared with the tube body with a short rigid segment, the distal end of the tube body with this structure has a larger radius of deflection, which influences the flexibility of the sheath tube during pushing; if the radius of deflection is large in the lumen of the human body lumen with small space, there is not enough space available for bending the sheath tube.

SUMMARY OF THE PRESENT INVENTION

To address the defects of the prior art, a technical problem to be solved by the present invention is to provide an adjustable bend sheath tube.

A technical solution adopted by the present invention to solve the technical problem is that an adjustable bend sheath tube is provided, including a tube body, a traction mechanism and a fixing and connecting mechanism; the traction mechanism includes an anchor ring and a traction wire; the anchor ring is coaxially embedded in a distal elastic segment of the tube body; the traction wire is arranged in a side wall of the tube body, and extends along the axial direction of the tube body; the traction wire includes a first segment and a second segment connected to each other, wherein the first segment near a proximal end of the tube body is connected to the fixing and connecting mechanism, and the second segment hooks the anchor ring.

In the adjustable bend sheath tube according to an embodiment of the present invention, the second segment is bent at a distal end surface of the anchor ring, and extends towards the proximal end of the tube body and is fixed to the fixing and connecting mechanism.

In the adjustable bend sheath tube according to the embodiment of the present invention, the side wall of the tube body is provided with two traction wire channels which are parallel to each other and extend along the axial direction of the tube body, the traction wire is accommodated in the two traction wire channels.

In the adjustable bend sheath tube according to the embodiment of the present invention, the second segment, after being bent at the distal end face of the anchor ring, is fixedly connected to the anchor ring.

In the adjustable bend sheath tube according to the embodiment of the present invention, the second segment is fixedly connected to the anchor ring by welding or by adhesive.

In the adjustable bend sheath tube according to the embodiment of the present invention, the second segment, after being bent at the distal end face of the anchor ring, is fixedly connected to the first segment.

In the adjustable bend sheath tube according to the embodiment of the present invention, the second segment is fixedly connected to the first segment by a steel sleeve, a heat shrink tube, welding or adhesive.

In the adjustable bend sheath tube according to the embodiment of the present invention, the second segment, after being bent at the distal end surface of the anchor ring, hooks a proximal end surface of the anchor ring.

In the adjustable bend sheath tube according to the embodiment of the present invention, one portion of the second segment for hooking the anchor ring is treated by annealing at 300° C. to 500° C.

In the adjustable bend sheath tube according to the technical solution of the present invention, the traction wire hooks the anchor ring, so that a force bearing point between the anchor ring and the traction wire is a hooked portion between the anchor ring and the traction wire. This connection method is similar to a flexible connection, which can ensure the connection strength and the connection stability between the traction wire and the anchor ring. In addition, the traction mechanism has a simple structure without additional components or additional modified structure itself, but only changes the connection method between the traction wire and the anchor ring, so that it does not need to increase the sizes of the anchor ring and the traction wire, and will not have a significant influence on the wall thickness of the tube body.

BRIEF DESCRIPTION OF THE DRAWINGS

The present invention will be further illustrated below with reference to the accompanying drawings and embodiments, in the drawings.

DETAILED DESCRIPTION OF THE PRESENT INVENTION

In order to understand the technical characteristics, the objects and the effects of the present invention more clearly, the specific implementation ways of the present invention will be described in detail with reference to the accompanying drawings.

With reference to FIG. 1 to FIG. 5, an adjustable bend sheath tube 100 according to a first embodiment of the present invention is provided, including a tube body 110, a traction mechanism 120, a fixing and connecting mechanism 130 and a handle 140. A proximal end of the tube body 110 is fixedly connected to the handle 140; the traction mechanism 120 extends along the axial direction, and is embedded in a side wall of the tube body 110. The traction mechanism 120 is fixedly connected to the fixing and connecting mechanism 130 in the handle 140 near the proximal end of the tube body 110.

The tube body 110 includes a distal elastic segment 111 and a proximal rigid segment 112 with different modulus of elasticity, and the proximal rigid segment 112 is fixedly connected to the handle 140. The tube body 110 includes an inner layer 113, an intermediate layer 114 surrounding the inner layer 113, and an outer layer 115 in the radial direction from the inside to the outside; the inner layer 113 is made of Polytetrafluoroethylene, the intermediate layer 114 is a metal spring tube or woven mesh tube, and the outer layer 115 is made of thermoplastic plastic including nylon, polyether-polyamide block copolymer and the like. During over-molding, the thermoplastic material of the outer layer 115 is melted to be fully combined with the PTFE of the inner layer 113 to form the tube body 110. The inner layer 113 is encircled to form an inner delivery cavity 117 which extends continuously through the tube body 110 from the distal end to the proximal end; the inner layer 113, the intermediate layer 114 and the outer layer 115 form a side wall of the tube body 110.

The traction mechanism 120 comprises an anchor ring 121 and a traction wire 122. The anchor ring 121 is coaxially embedded in the side wall of the distal elastic segment 111, and encircles the inner layer 113; the traction wire 122 is arranged in the side wall of the tube body 110, and extends along the axial direction of the tube body 110. One segment of the traction wire 122 hooks the anchor ring 121, and another segment thereof is connected to the fixing and connecting mechanism 130. For example, the traction wire 122 passes through a ring wall of the anchor ring 121 to hook the anchor ring 121, or can be bent to stride over a distal end surface of the anchor ring 121 to hook the anchor ring 121. Preferably, the traction wire 122 hooks the anchor ring 121 in a distal region of the anchor ring 121.

Specifically, the traction wire 122 includes a first traction wire segment 122a and a second traction wire segment 122b which are axially parallel with each other, and a bending portion 122c connecting the distal end of the first traction wire segment 122a and the distal end of the second traction wire segment 122b. The first traction wire segment 122a and the second traction wire segment 122b both extend along the axial direction to pass through the side wall, and are connected to the fixing and connecting mechanism 130 in the handle 140 near the proximal end of the tube body 110; the first traction wire segment 122a and the second traction wire segment 122b are respectively located on two opposite sides (inner side and outer side) of the anchor ring 121. The bending portion 122c strides over the distal end surface of the anchor ring 121 to hook the anchor ring 121.

The anchor ring 121 may be made of stainless steel, platinum, gold, tungsten, tantalum and other heavy metals or their alloys with a thickness of about 0.05 mm to 0.30 mm. The anchor ring 121 is coaxially and annularly sleeved on the outer wall of the inner layer of 113, the second traction wire segment 122b passes through a gap between the inner side of the anchor ring 121 and the inner layer 113, and the first traction wire segment 122a passes through the outer side of the anchor ring 121, and enables the bending portion 122c to closely attach to the anchor ring 121; the first traction wire segment 122a and the second traction wire segment 122b are kept aligned with each other.

The traction wire 122 may be a round or flat metal wire with a diameter of about 0.05 to 0.25 mm, and a length of the traction wire 122 is at least twice of the axial length of the tube body 110, and the traction wire 122 may be a stainless steel wire, tungsten alloy steel wire, cobalt chromium alloy steel wire or nickel titanium alloy steel wire and the like. When the traction wire 122 is to be bent to form the bending portion 122c, the portion to be bent is first subjected to an annealing treatment at an annealing temperature chosen based on the material of the metal wire, and then the traction wire 122 is bent by 135 to 225 degrees, to form a circular arc bending portion 122c with a radius of curvature of about 0.1 mm to 0.4 mm.

Figure 6:
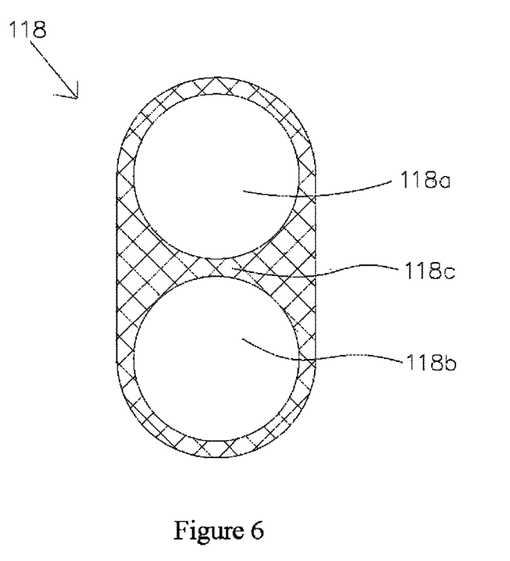
FIG. 6 is a schematic cross section of a traction wire tube of the adjustable bend sheath tube in FIG. 1.

With reference to FIG. 2 to FIG. 5, a traction wire tube 116 configured to accommodate the traction wire 122 is also arranged in the side wall of the tube body 110, and the cavity wall thereof is made of PTFE. The traction wire tube 116 is arranged between the inner layer 113 and the intermediate layer 114, and may be fixed on the inner layer 113 by welding, bonding or fusion welding. In the axial direction, the traction wire tube 116 extends near the proximal end of the anchor ring 121 and the proximal end of the tube body 110. Here, the tube body 110 includes two independent and axially parallel traction wire channels 116a and 116b. Alternatively, with reference to FIG. 6, the traction wire tube 118 includes a first traction wire channel 118a and a second traction wire channel 118b which are axially parallel with each other, and a traction wire tube wall 118c which is enclosed to form the first traction wire channel 118a and the second traction wire channel 118b. The traction wire tube wall 118c is made of PTFE.

Figure 1:
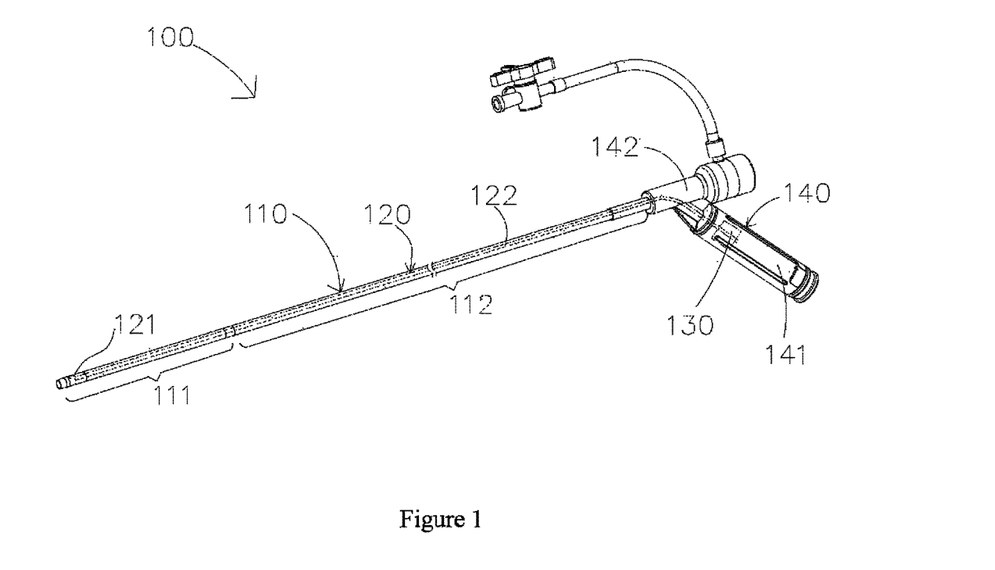
FIG. 1 is a schematic diagram of an adjustable bend sheath tube of a first embodiment of the present invention.
Figure 2:
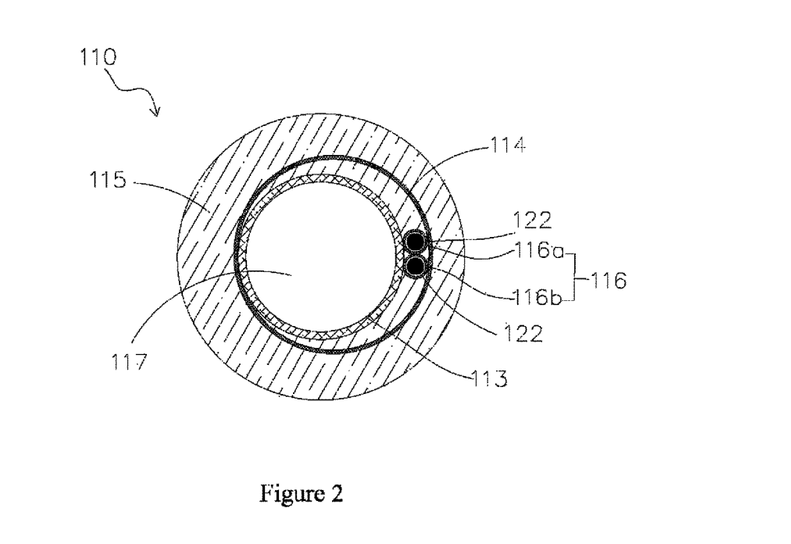
FIG. 2 is a schematic cross section of a tube body of the adjustable bend sheath tube in FIG. 1.
Figure 3:
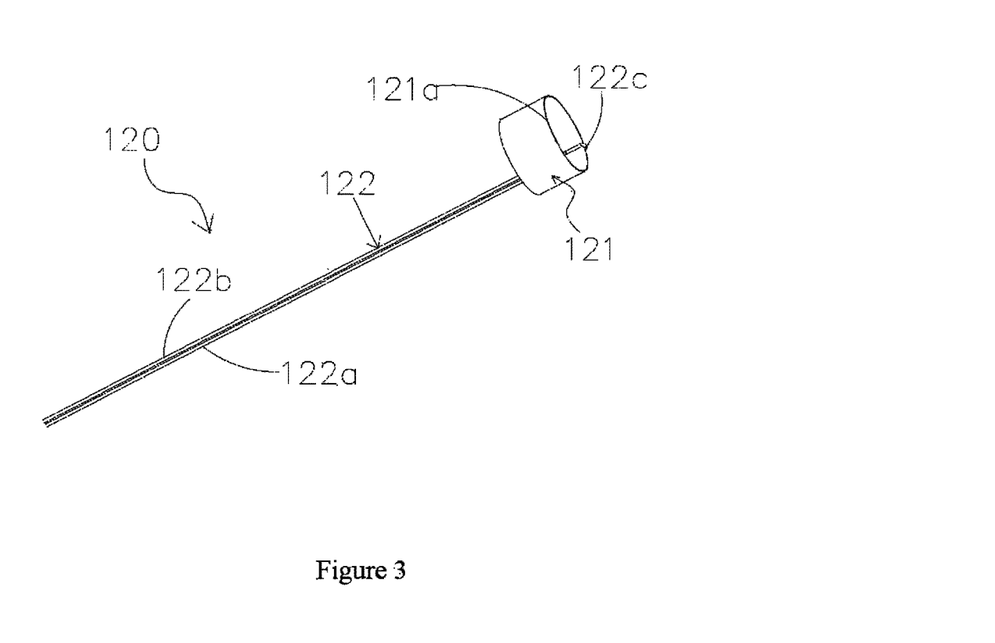
FIG. 3 is a schematic diagram of a traction mechanism and a fixing and connecting mechanism of the adjustable bend sheath tube in FIG. 1.
Figure 4:
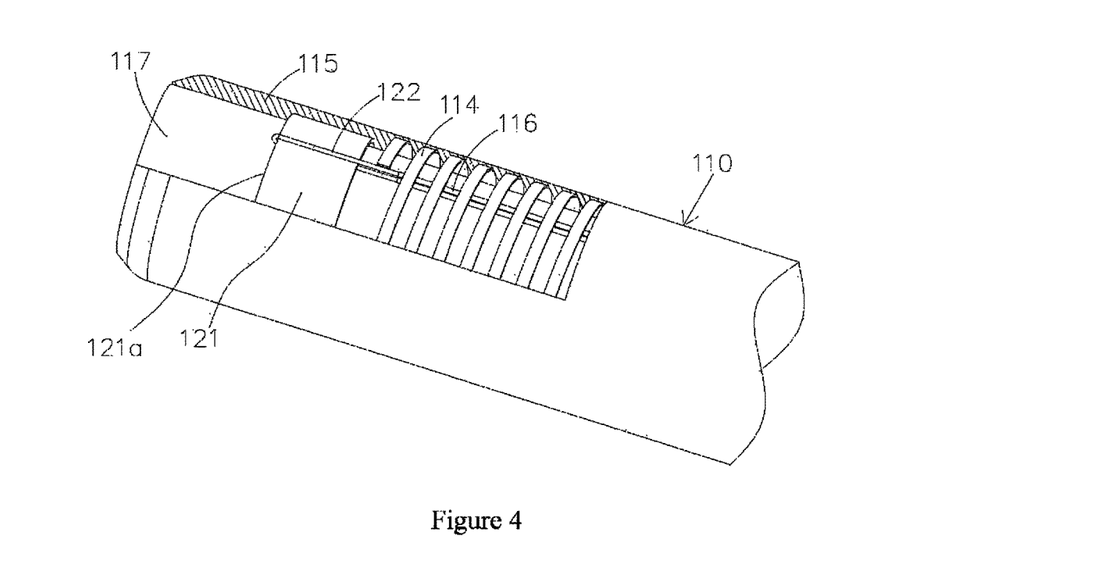
FIG. 4 is a partial sectional view of the adjustable bend sheath tube in FIG. 1.
Figure 5:
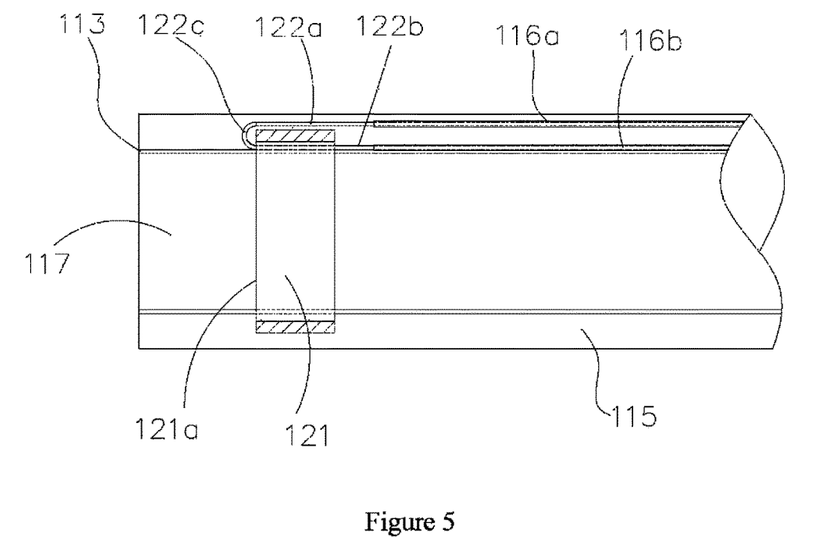
FIG. 5 is a partial section view of the adjustable bend sheath tube in FIG. 1.
Figure 7:
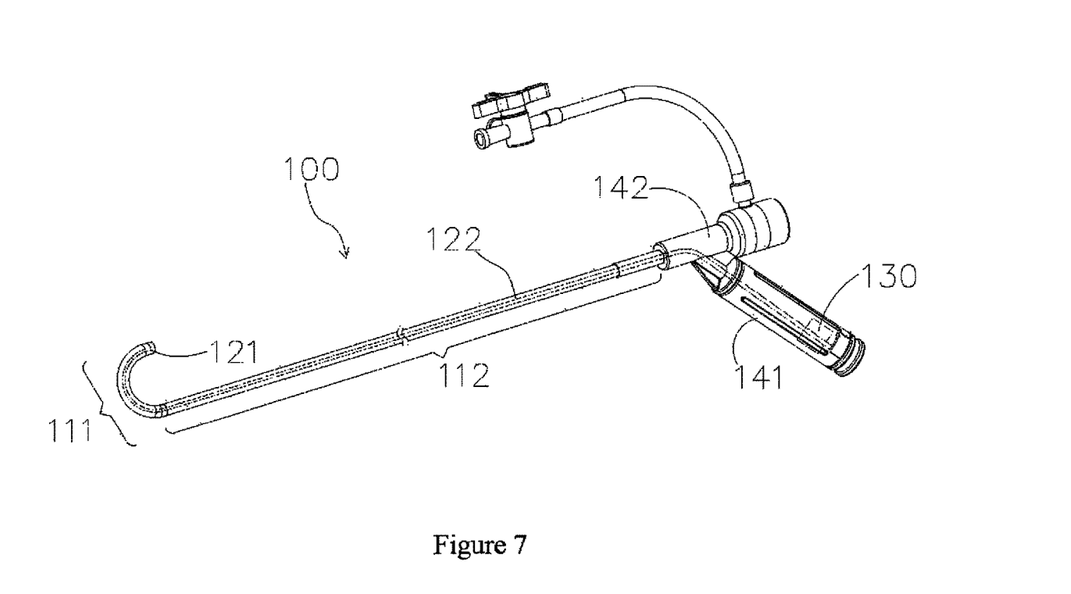
FIG. 7 is a schematic diagram of the adjustable bend sheath tube in FIG. 1 during adjustable bending.
Figure 9:
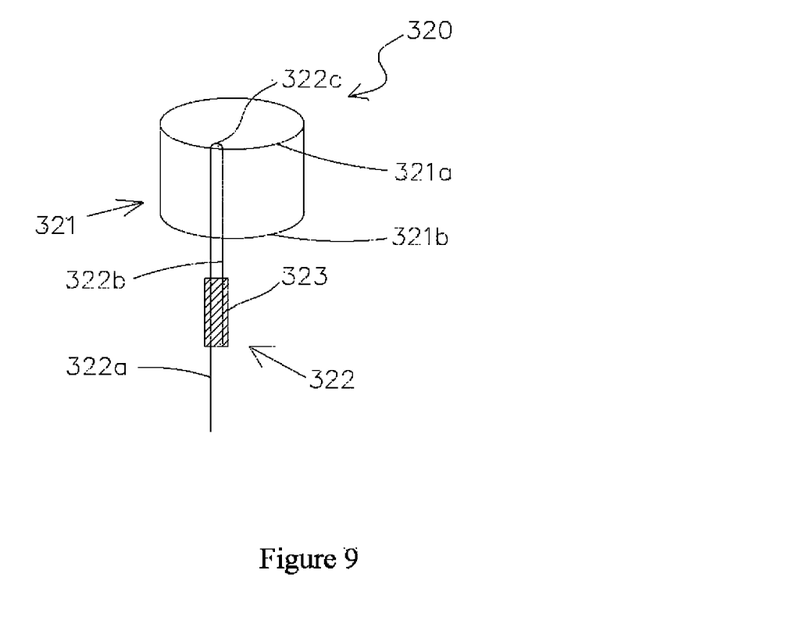
FIG. 9 is a schematic diagram of a traction mechanism of an adjustable bend sheath tube of a third embodiment of the present invention.

With reference to FIG. 1 and FIG. 7, in an adjustable bending process of the adjustable bend sheath tube 100, the fixing and connecting mechanism 130 in a rotary knob 141 is moved by any existing appropriate way, and transfers the force and displacement to the traction wire 122 to drive the traction wire 122 to axially move relative to the tube body 110, and then transfers the force and displacement to the anchor ring 121. The distal elastic segment 111 is driven by the anchor ring 121. Uneven deformation is generated due to different modulus of elasticity of the distal elastic segment 111 and the proximal rigid segment 112, so that the distal elastic segment 111 is bent (as shown in FIG. 9), thereby achieving adjustable bending of the sheath tube. In the adjustable bending process, the following key force bearing points exist: between the anchor ring 121 and the traction wire 122, and the traction wire 122 itself. The tensile strength and fatigue strength of the force bearing points determine the validity and reliability of the force and displacement.

The traction wire 122 hooks the distal end face 121a of the anchor ring 121 through the bending portion 122c thereof. Therefore, the force bearing points between the anchor ring 121 and the traction wire 122 are the bending portion 122c and the distal end face 121a. This connection method is similar to the flexible connection, which may ensure connection strength and stability. Moreover, after the annealing treatment, the tensile strength and the fatigue strength of the bending portion 122c are essentially not changed; the bending portion 122c having been adjustably bent still has better bending property and fatigue performance; the strength between the anchor ring 121 and the traction wire 122 is basically the same as that of the traction wire 122 itself, which is no longer a weak force bearing point. Compared with the direct welding connection method between the anchor ring and the traction wire, this connection method has the obvious advantage in stability. In addition, the traction mechanism has a simple structure, and only changes the structural arrangement of the traction wire 122 relative to the anchor ring 121 without additional components or additional modified structure itself. Therefore, on the premise of meeting the tensile strength and stability, there is no need to increase the sizes of the anchor ring 121 and the traction wire 122. Regarding the thickness of the side wall of the tube body 110, it is only necessary to increase the diameter of the traction wire. In this way, the traction mechanism 120 may be fully embedded by using a thinner plastic outer layer 115, thereby effectively reducing the influence on the wall thickness by the traction mechanism 120.

In addition, in this embodiment, the traction wire 122 is bent into two axially parallel segments, correspondingly, two traction wire channels for accommodating the first traction wire segment 122a and the second traction wire segment 122b, respectively, are arranged in the side wall, in order to avoid the traction wire segments entangling. Moreover, the first traction wire segment 122a and the second traction wire segment 122b during adjustable bending decompose the tensile force, so that the tensile strength of the traction wire 122 per unit cross-sectional area may be improved; on the premise of ensuring the same tensile strength, the diameter of the traction wire 122 may be decreased, thereby reducing the side wall thickness of the tube body 110.

Figure 8:
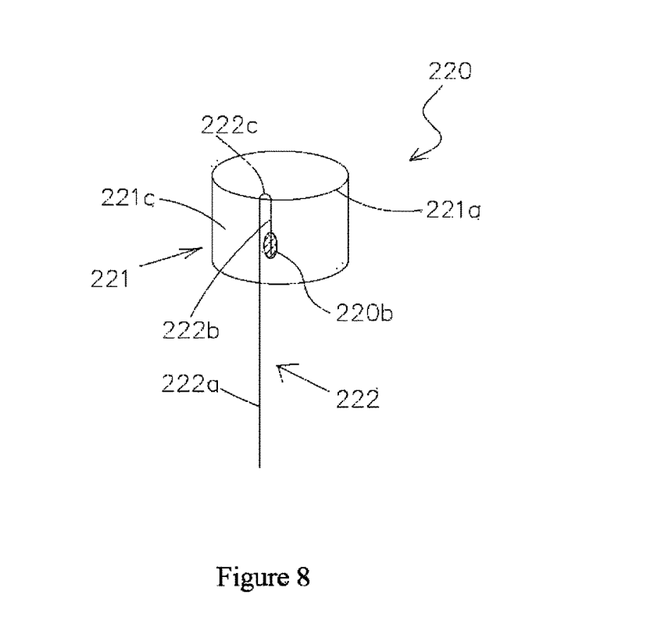
FIG. 8 is a schematic diagram of a traction mechanism of an adjustable bend sheath tube of a second embodiment of the present invention.

With reference to FIG. 8, different from the adjustable bend sheath tube 100 mentioned above, a proximal end of a second traction wire segment 222b of a traction mechanism 220 according to a second embodiment of the present invention is fixed on an anchor ring 221, preferably fixed on a ring surface 221c of the anchor ring 221; e.g. an inner ring surface to form a connection point 220b, and may be fixed by welding or gluing. A first traction wire segment 222a is pulled, the force bearing points between a traction wire 222 and the anchor ring 221 are still a bending portion 222c and a distal end face 221a, which may also ensure the tensile strength and stability. Meanwhile, the second traction wire segment 222b terminates on the anchor ring 221, and so there is no need for the two traction wire segments 222a and 222b to extend at the same time to pass through the side wall, thereby decreasing the side wall thickness. Furthermore, the difficulty for manufacturing the tube body is simplified without the need for two traction wire channels.

With reference to FIG. 9, different from the adjustable bend sheath tube 100 mentioned above, a second traction wire segment 322b of a traction mechanism 320 according to a third embodiment of the present invention is fixedly connected to a first traction wire segment 322a parallel with the second traction wire segment 322b near a proximal end surface 321b of an anchor ring 321. The two traction wire segments 322a and 322b are fixedly connected by a steel sleeve, a heat shrink tube, welding or adhesive, and FIG. 9 shows that the two traction wire segments 322a and 322b are fixedly connected by the clamping by a steel sleeve 323. When a first traction wire segment 322a is pulled, the force bearing points between a traction wire 322 and the anchor ring 321 are still a bending portion 322c and a distal end face 321a, which may also ensure the tensile strength and stability. Meanwhile, the second traction wire segment 322b terminates near the anchor ring 321, and so there is no need for the two traction wire segments 322a and 322b to extend at the same time to pass through the side wall, thereby decreasing the side wall thickness. Furthermore, the difficulty for manufacturing the tube body is simplified without the need for two traction wire channels.

Figure 10:
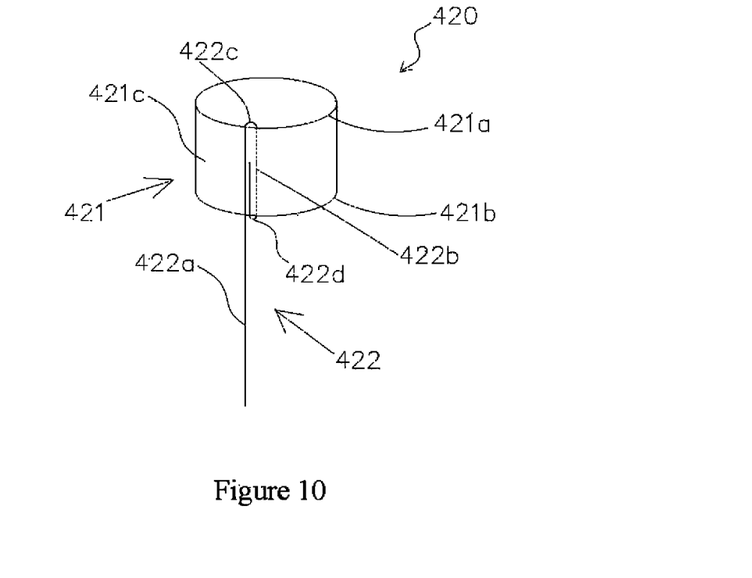
FIG. 10 is a schematic diagram of a traction mechanism of an adjustable bend sheath tube of a fourth embodiment of the present invention.

With reference to FIG. 10, different from the adjustable bend sheath tube 100 mentioned above, a second traction wire segment 422b of a traction mechanism 420 according to a fourth embodiment of the present invention is bent to stride over a proximal end face 421b of an anchor ring 421 so as to hook the proximal end face 421b. Here, a second bending portion 422d is formed, and then extends towards a distal end surface 421a of the anchor ring 421 and is closely attached to a ring surface 421c of the anchor ring 421. Here, the second traction wire segment 422b is fixed without an additional fixing operation (e.g. welding or gluing) or fixing component (e.g. steel sleeve). In the over-molding process of the outer layer of the tube body, the laminating effect thereof may firmly attach the second traction wire segment 422b to the anchor ring 421. And, because of the second bending portion 422d, the pull force applied on a traction wire 422 is rarely transferred to a free end of the second traction wire segment 422b closely attached to the anchor ring 421; the force bearing points between the traction wire 422 and the anchor ring 421 are still the first bending portion 422c and a distal end face 421a, thus ensuring the tensile strength.

The above descriptions are merely preferred embodiments of the present invention, but not for limiting the present invention. Any modification, equivalent replacement and improvement done within the spirit and principle of the present invention should be regarded as falling into the protection scope of the present invention.

The invention claimed is:

1. An adjustable bend sheath tube, comprising a tube body having a distal end and a proximal end, a traction mechanism and a fixing and connecting mechanism; the traction mechanism comprising an anchor ring and a traction wire; the anchor ring being coaxially embedded in a distal elastic segment of the tube body; the traction wire being arranged in a side wall of the tube body, and extending along the axial direction of the tube body; the traction wire comprising a first segment and a second segment which are axially parallel with each other, the first and second segments having a distal end that are connected to each other by a bending portion, with the first segment connected to the fixing and connecting mechanism near the proximal end of the tube body, and with the bending portion extending around the anchor ring to hook the anchor ring, wherein the tube body is provided with first and second independent traction wire channels which are parallel to each other and extend along the axial direction of the tube body, each traction wire channel having a lumen defined by a luminal wall, with the first segment of the traction wire extending inside the first traction wire channel and the second segment of the traction wire extending inside the second traction wire channel, wherein the first and second segments are separated by the luminal walls of the first and second traction wire channels;

wherein the first and second traction wire channels are positioned side-by-side from the proximal end of the tube body to the distal end of the tube body along a same side of the tube body.

2. The adjustable bend sheath tube according to claim 1, wherein the second segment extends towards the proximal end of the tube body and is fixed to the fixing and connecting mechanism.

3. The adjustable bend sheath tube according to claim 2, wherein the bending portion has a radius of curvature that is in a range from 0.1 mm to 0.4 mm.

4. The adjustable bend sheath tube according to claim 2, wherein the tube body comprises an inner layer, an intermediate layer surrounding the inner layer, and an outer layer in the radial direction from inside to outside, the luminal walls of the first and second traction wire channels are sandwiched between the inner layer and the intermediate layer, and are fixed on the inner layer.

5. The adjustable bend sheath tube according to claim 2, wherein one portion of the second segment for hooking the anchor ring is treated by annealing at 300° C. to 500° C.

6. The adjustable bend sheath tube according to claim 1, wherein the bending portion has a radius of curvature that is in a range from 0.1 mm to 0.4 mm.

7. The adjustable bend sheath tube according to claim 6, wherein the tube body comprises an inner layer, an intermediate layer surrounding the inner layer, and an outer layer in the radial direction from inside to outside, the luminal walls of the first and second traction wire channels are sandwiched between the inner layer and the intermediate layer, and are fixed on the inner layer.

8. The adjustable bend sheath tube according to claim 7, wherein one portion of the second segment for hooking the anchor ring is treated by annealing at 300° C. to 500° C.

9. The adjustable bend sheath tube according to claim 1, wherein the tube body comprises an inner layer, an intermediate layer surrounding the inner layer, and an outer layer in the radial direction from inside to outside, the luminal walls of the first and second traction wire channels are sandwiched between the inner layer and the intermediate layer, and are fixed on the inner layer.

* * * * *